US00PP24269P3

(12) United States Plant Patent
Nielsen

(10) Patent No.: US PP24,269 P3
(45) Date of Patent: Feb. 25, 2014

(54) *OSTEOSPERMUM* PLANT NAMED 'DAOSTOOGTYVE'

(50) Latin Name: *Osteospermum ecklonis*
Varietal Denomination: DAOSTOOGTYVE

(75) Inventor: Rune Harboe Nielsen, Grönnegyden (DK)

(73) Assignee: Dalina Genetics ApS, Odense N (DK)

( * ) Notice: Subject to any disclaimer, the term of this patent is extended or adjusted under 35 U.S.C. 154(b) by 91 days.

(21) Appl. No.: 13/506,396

(22) Filed: Apr. 17, 2012

(65) Prior Publication Data

US 2013/0276189 P1 Oct. 17, 2013

(51) Int. Cl.
*A01H 5/00* (2006.01)

(52) U.S. Cl.
USPC ..... Plt./360

(58) Field of Classification Search
USPC ..... Plt./360
See application file for complete search history.

(56) References Cited

PUBLICATIONS

Printout of application information from Community Plant Variety Office (CPVO) website for corresponding CPVO application No. 2011/1944 filed Aug. 9, 2011 (1 page) (http://www.cpvoextranet.cpvo.europa.eu).

Printout of application information for Canadian Plant Breeders' Rights application No. 11-7385 filed Oct. 6, 2011, published in Plant Varieties Journal No. 82, Jan. 2012 (1 page) (www.inspection.gc.ca/plants/plant-breeders-rights/plant-varieties-journal).

*Primary Examiner* — Susan McCormick Ewoldt
(74) *Attorney, Agent, or Firm* — Foley & Lardner LLP

(57) ABSTRACT

A new and distinct cultivar of *Osteospermum* plant named 'DAOSTOOGTYVE', characterized by its vigorous growth, with globular upright to spreading shape; well branching (3-5 per plant) habit, with stiff and strong lateral stems and thick leaves; color of leaves RHS 139A (upper side), RHS 137B (Underside); ray florets with a unique color combination, RHS Purple N78C, the inner third is grading into white on the upperside; stripes in various violet colors like RHS Violet 85A to Violet 86A on the underside; and Disk florets that appear RHS Violet-blue 93A.

6 Drawing Sheets

Latin name of the genus and species of the claimed plant: *Osteospermum ecklonis*.

Variety denomination: 'DAOSTOOGTYVE'.

BACKGROUND OF THE INVENTION

The present invention relates to a new and distinct cultivar of *Osteospermum* plant, botanically known as *Osteospermum ecklonis* (DC) T Norl., commonly known as Cape Daisy and and hereinafter referred to by the cultivar name 'DAOSTOOGTYVE'.

The new *Osteospermum* cultivar is a product of a planned breeding program conducted by the inventor, Rune Nielsen, in Stige, Denmark. The objective of the breeding program is to develop a new *Osteospermum* cultivar with good garden performance, well branching growth, continuous flowering and an attractive inflorescence color.

The new *Osteospermum* cultivar originated from a cross, made in a controlled breeding program by the inventor in 2007, in Stige, Denmark. The female or seed parent is a white/purple *Osteospermum* variety designated 5781C (not patented). The male or pollen parent is a dark purple colored *Osteospermum* cultivar named 'Sunny Mary' (U.S. Plant Pat. No. 16,389 P13).

Asexual reproduction of the new *Osteospermum* cultivar by terminal cuttings was first performed in November, 2008 in Stige, Denmark, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'DAOSTOOGTYVE', which in combination distinguish this *Osteospermum* as a new and distinct cultivar:

1. Vigorous cultivar, with globular upright to spreading shape;
2. Well branching (3-5 per plant) with 5 mm thick, stiff and strong lateral stems (2-5 per basal branch) and thick leaves. Color of mature leaves RHS 139A (upper side) RHS 137B (Underside);
3. Ray florets with a unique color combination, RHS Purple N78C. The inner third is grading into white on the upperside. Stripes in various violet colors like RHS Violet 85A to Violet 86A on the underside; and
4. Disk florets that appear Violet-blue 93A.

Plants of the new *Osteospermum* 'DAOSTOOGTYVE' differ from plants of the parents, 5781C (unpatented) and 'Sunny Mary' (U.S. Plant Pat. No. 16,389 P13) in the traits described in Table 1.

TABLE 1

| Comparison with Parent Varieties | | | |
|---|---|---|---|
| Trait | New Cultivar 'DAOSTOOGTYVE' | Female Parent 5781C (unpatented and no longer available) | Male Parent 'Sunny Mary' (U.S. Plant Pat. No. 16,389 P13) |
| Plant Size | | | |
| Height: | 15-17 cm. | About 17 cm. | 15-17 cm. |
| Diameter: | 18-24 cm. | About 20 cm. | 18-24 cm. |
| Overall Plant Shape: | Globular, upright to spreading, with basal and lateral branching. | Globular, upright to spreading, with basal and lateral branching. | Globular, upright to spreading, with basal and lateral branching. |
| Basal branches | | | |
| Length (incl. flowers): | 17-20 cm. | About 7 cm. | 17-20 cm. |
| Diameter: | 5 mm | About 3 mm. | 5 mm |
| Strength: | Stiff and strong. | Medium strong. | Stiff and strong. |
| Color: | RHS 144A. | | RHS 144A. |
| Number of Inflorescence heads per Plant (buds and open flowers): | About 32. | About 30. | About 35. |
| Flower Size | | | |
| Diameter: | About 7.5 cm. | About 7 cm. | About 5.5-6 cm. |
| Mature Petal Color (upper surface): | RHS Purple N78C. The inner third is grading into white. | Purple white at the base. | RHS Red-purple 72A. |

Of the many commercial cultivars known to the present inventor, the most similar in comparison to the new *Osteospermum* 'DAOSTOOGTYVE' is the *Osteospermum* cultivar 'Cape Daisy® Zanzibar Pink', in the characteristics described in Table 2:

TABLE 2

| Comparison with Similar Variety | | |
|---|---|---|
| Trait | New Cultivar 'DAOSTOOGTYVE' | Comparison Cultivar 'Cape Daisy ® Zanzibar Pink' |
| Plant Size | | |
| Height: | 15-17 cm. | About 9 cm. |
| Diameter: | 18-24 cm. | About 16 cm. |
| Overall Plant Shape: | Globular, upright to spreading, with basal and lateral branching. | Globular, upright to spreading, with basal and lateral branching. Lateral branching near top of plant. |
| Basal branches | | |
| Length (incl. flowers): | 17-20 cm. | About 16-19 cm. |
| Diameter: | 5 mm | About 4 mm. |
| Strength: | Stiff and strong. | Medium strong. |
| Color: | RHS 144A. | RHS 144A. |
| Number of Inflorescence heads per Plant (bud sand open flowers): | About 32. | About 40. |

TABLE 2-continued

| Comparison with Similar Variety | | |
|---|---|---|
| Trait | New Cultivar 'DAOSTOOGTYVE' | Comparison Cultivar 'Cape Daisy ® Zanzibar Pink' |
| Flower Size | | |
| Diameter: | About 7.5 cm. | About 6.5 cm. |
| Mature Petal Color (Upper surface): | RHS Purple N78C. The inner third is grading into white. | RHS Purple N78C. The inner third is grading into white. The inner 2 mm near base is RHS Purple 79A. |
| Mature Petal Color (Underside): | Stripes in various violet colors RHS Violet 85A to Violet 86A. | RHS 83D with stripes of RHS 83B. |

BRIEF DESCRIPTION OF THE PHOTOGRAPHS

The accompanying photographs illustrate the overall appearance of the new *Osteospermum* 'DAOSTOOGTYVE' showing the colors as true as is reasonably possible with colored reproductions of this type. Colors in the photographs may differ slightly from the color value cited in the detailed botanical description, which accurately describe the color of 'DAOSTOOGTYVE'.

Figure 1:
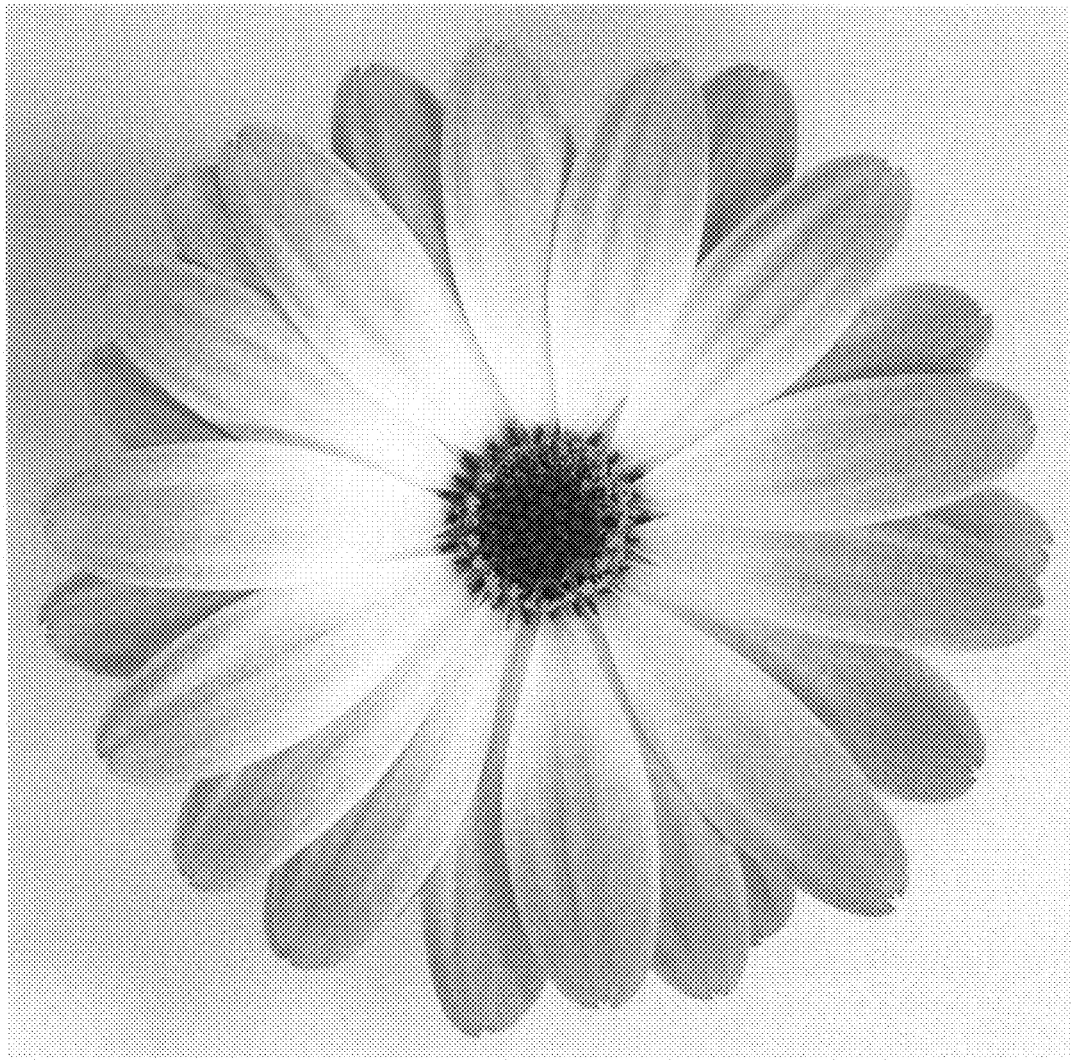
FIG. 1 shows a close-up view of the composite flower head from 'DAOSTOOGTYVE'.
Figure 2:
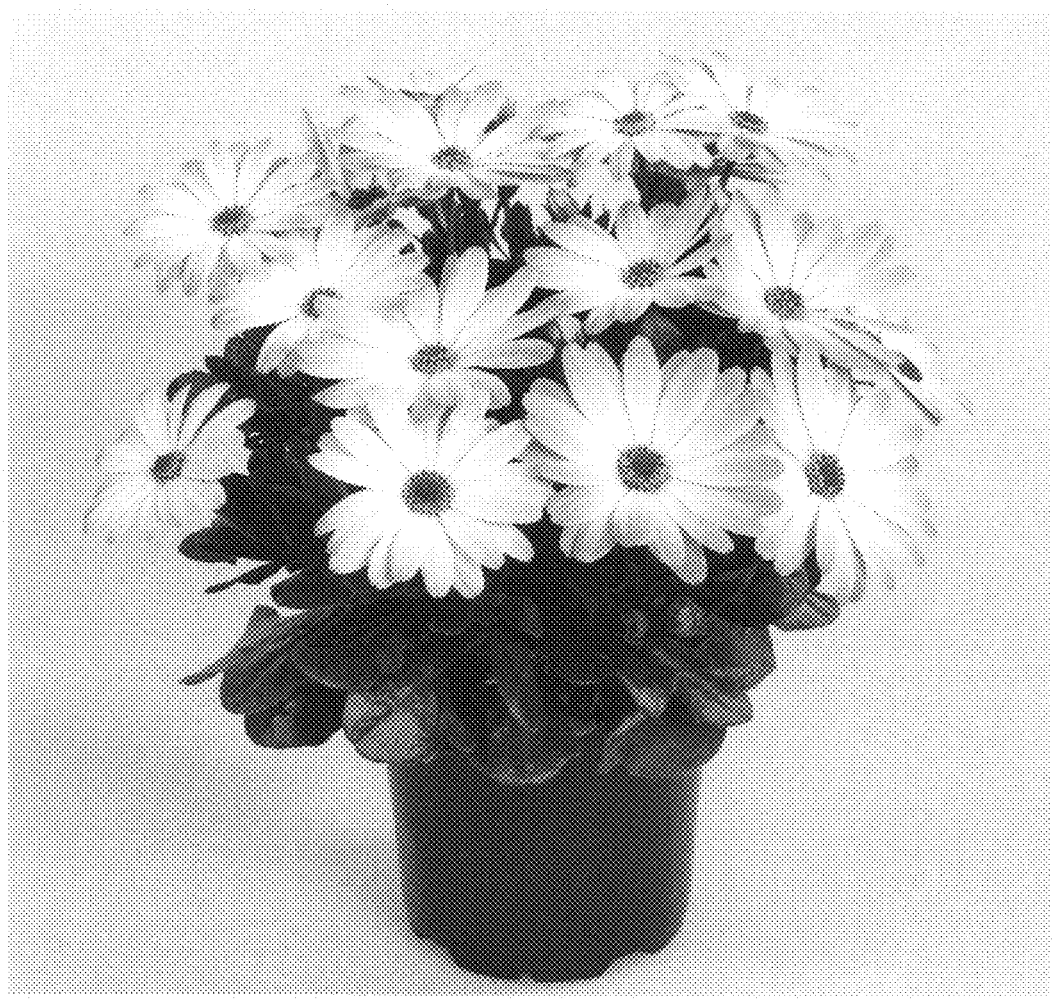
FIG. 2 shows a side view perspective of a typical flowering plant of 'DAOSTOOGTYVE' in a 11 cm pot, at 12 weeks of age after planting.
Figure 3:
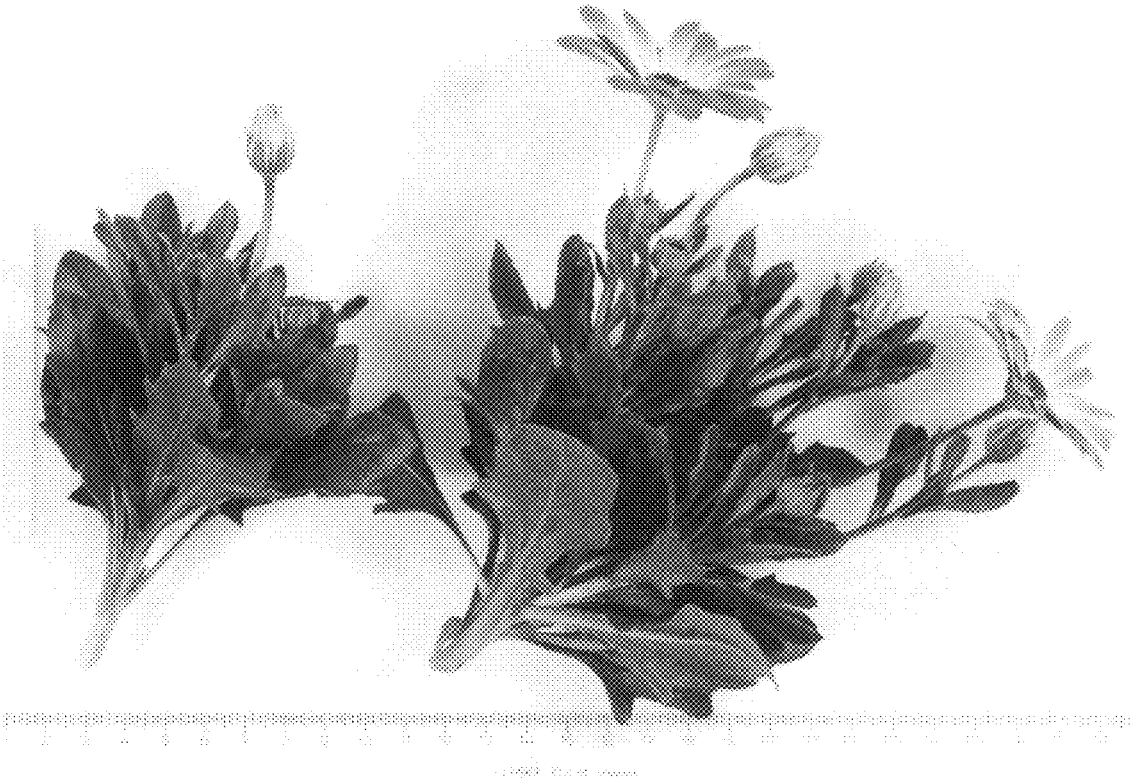
FIG. 3 shows a close-up view of the typical lateral stems with leaves and buds of 'DAOSTOOGTYVE'.
Figure 4:
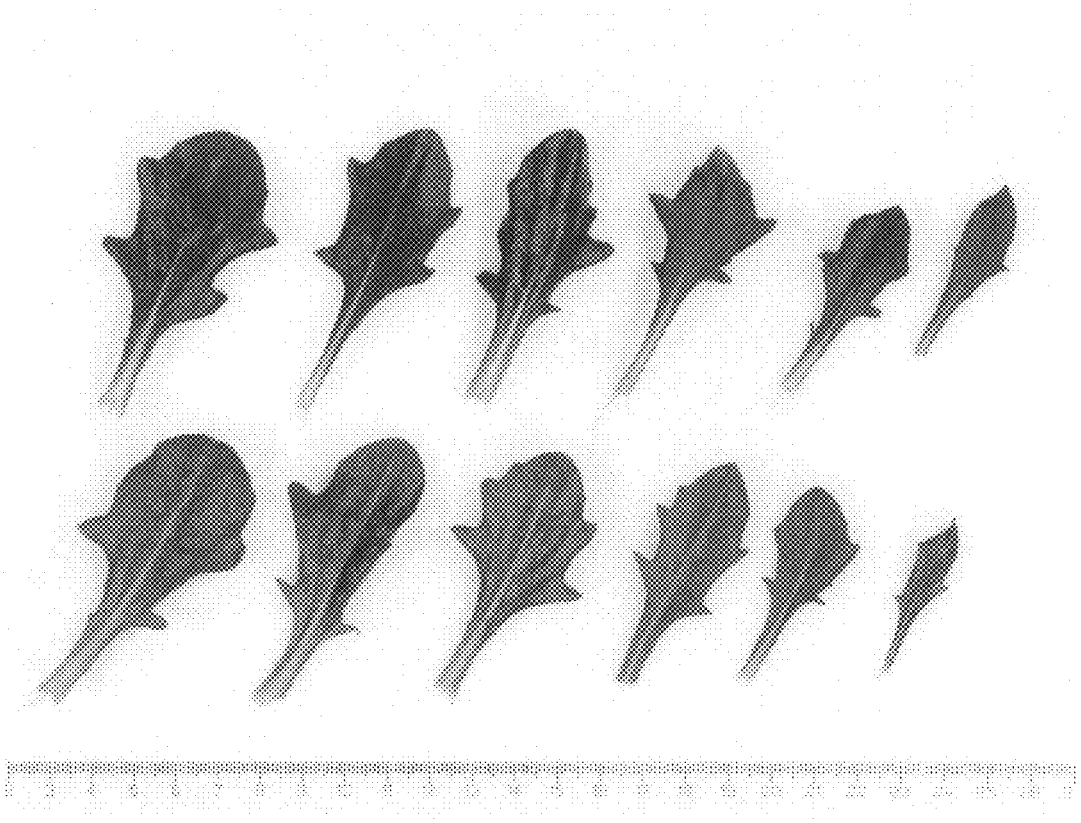
FIG. 4 shows a close-up view of the different leaf sizes of 'DAOSTOOGTYVE'.
Figure 5:
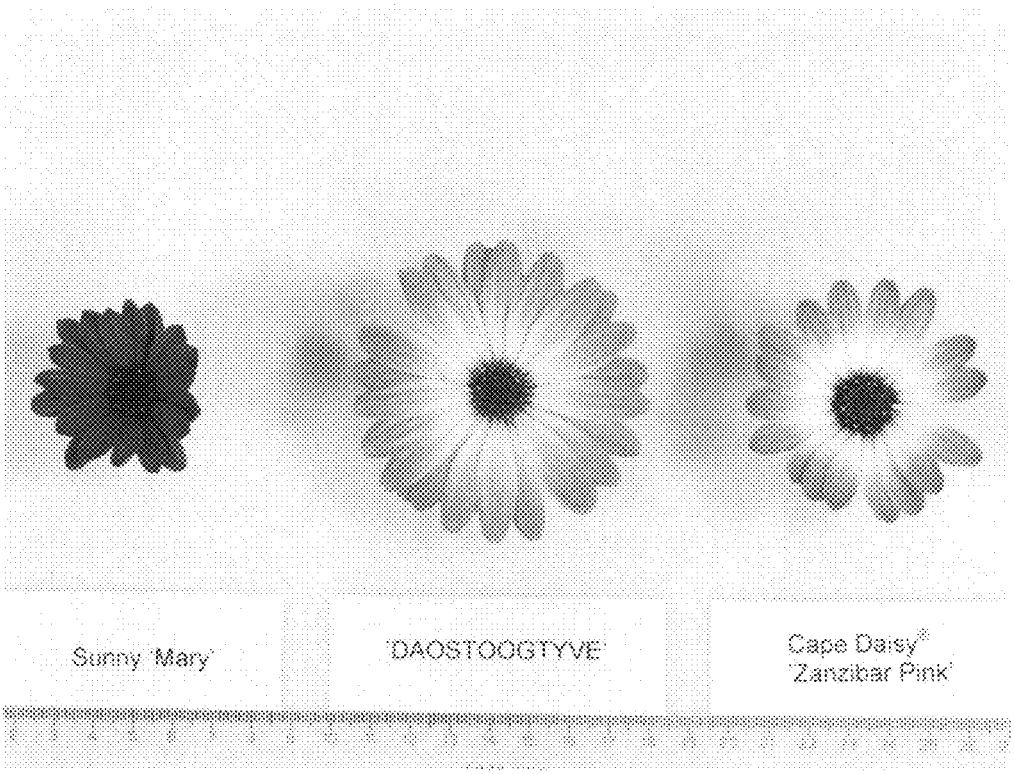

FIG. 5 shows a comparison between the upperside of the flowers from 'Sunny Mary' (U.S. Plant Pat. No. 16,389 P13), 'DAOSTOOGTYVE' (Breeders reference: 6405H) and 'CAPE DAISY Zanzibar Pink'.

Figure 6:
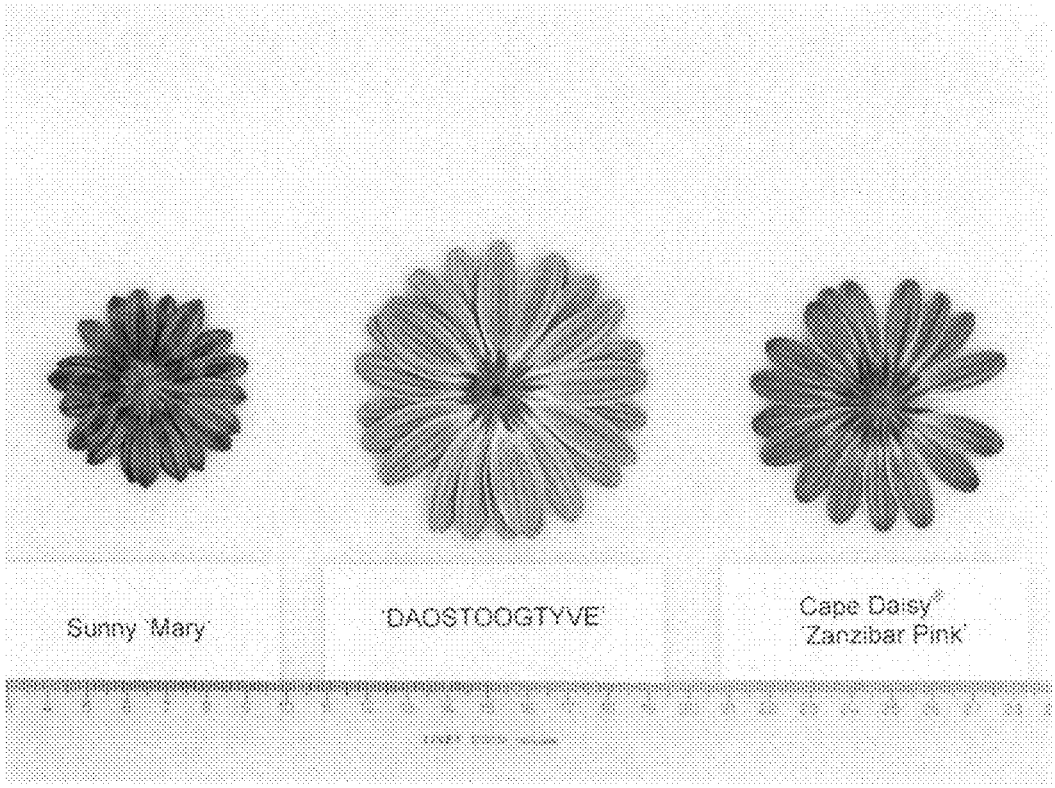

FIG. 6 shows a comparison between the underside of the flowers from 'Sunny Mary' (U.S. Plant Pat. No. 16,389 P13), 'DAOSTOOGTYVE' (Breeders reference: 6405H) and 'CAPE DAISY Zanzibar Pink'.

DETAILED BOTANICAL DESCRIPTION

The new *Osteospermum* 'DAOSTOOGTYVE' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Osteospermum* 'DAOSTOOGTYVE' as grown in a glasshouse, equipped with heat, assimilation light and ebb/flood watering system in Odense, Denmark, under conditions which closely approximate those generally used in commercial practice. The plants was grown in 14° C., with a venting temperature on 16° C. Assimilation light was given when natural daylight was below 3000 lux and the day length was extended to 16 hours. The EC (mS/m) levels in the soil were kept at about 2.5-3.5 and pH around 6.0 during the production. Plant growth was regulated 3 times during the production period, using 3% Cycocel (chlormequat-chloride) as a drench (80-100 ml/pot).

Color references are made to The Royal Horticultural Society Colour Chart (R.H.S.), Colour Chart 2001 edition, Color values were taken under March daylight conditions at approximately 10:00-14:00 in Stige, Denmark. The age of the 'DAOSTOOGTYVE' plants described is 12 weeks from potting.

Classification:

*Botanical.*—*Osteospermum ecklonis* (DC) Norl.

Parentage:

*Female or seed parent.*—*Osteospermum* plant designated 5781C (unpatented).

*Male or pollen parent.*—*Osteospermum* cultivar designated 'Sunny Mary' (U.S. Plant Pat. No. 16,389 P13).

Propagation:

*Type.*—Vegetative terminate cuttings.

*Time and temperature to initiate roots.*—About 9-13 days at 19-21° C. in tunnels in a greenhouse.

*Time and temperature to produce a rooted young plant.*—About 4-5 weeks at 18° (initiation period benefits from 19-21° C.).

*Rooting habit.*—Vigorous, white to grayed yellow and well branched.

Plant description:

*General appearance and form.*—Globular, upright to spreading, with basal branching. Inflorescences in composite heads. Freely branching with lateral flowering branches forming at nodes.

*Growth rate.*—Growing about 1 cm per week during production period.

*Plant height.*—About 15-17 cm.

*Plant width* (*spread*).—About 18-24 cm.

*Crop time to produce a mature flowering plant.*—It requires 4-5 weeks to produce a young plant in a 35 mm propagation plug. After potting 12-14 weeks are required to produce finished flowering plants in 11 cm pots.

Stem:

*Shape.*—Round.

*Length.*—About 2-4 cm.

*Diameter.*—About 6-7 mm.

*Strength.*—Stiff and strong.

*Aspect.*—Upright.

*Texture.*—Smooth and glabrous.

*Color.*—Yellow-green RHS 144A.

Branches:

*Branching habit.*—Basal branching with lateral branching.

*Number of basal branches per plant.*—About 3-5.

*Number of lateral branches per basal branch.*—2-5.

*Length* (*including flowers*).—About 17-20 cm.

*Diameter* (*basal branch*).—About 5 mm.

*Strength.*—Stiff and strong.

*Apect.*—Upright to spreading.

*Texture.*—Smooth and glabrous.

*Color.*—Mature: RHS 144A. Immature: RHS 144B.

*Internode length.*—About 3-10 mm.

*Internode color.*—RHS 144A.

Foliage description:

*Arrangement.*—Alternate.

*Number of leaves per branch.*—About 10-14 per branch.

*Length.*—About 5-8 cm.

*Width.*—About 2.5-4.0 cm.

*Overall shape of leaf.*—Obovate — spatulate with 2-5 acuminate teeth on some of the leaves.

*Shape at apex.*—Obtuse.

*Shape at base.*—Attenuate.

*Margin.*—Entire to dentate (2 lobes on each side of some of the leafs).

*Texture.*—Upper surface: Pubescent with few scattered short, stiff hairs. More hairs on the edges of leaf. Lower surface: Pubescent with few scattered short, stiff hairs More hairs along veins and on the edges of leaf.

*Color of developing foliage.*—Upper surface: RHS 137A. Lower surface: RHS 138A.

*Color of mature foliage.*—Upper surface: RHS 139A. Lower surface: RHS 137B.

*Venation pattern.*—Tri-nerved with veins along nerves.

*Venation color.*—Upper surface: RHS 145A. Lower surface: RHS 146C.

Inflorescence description:

*Arrangement and shape.*—Tubular disk floret and flat, lanceolate ray florets in composite flower heads, developed from terminal and axillary shoots. The peduncles lift the Inflorescences 3-5 cm above the foliage. Inflorescences face upright to 80° angle from vertical.

*Natural flowering season.*—*Osteospermum* is a bedding plant, with a flowering season from early spring to late autumn. Temperatures below 20° C. will increase flowering, temperatures above 20° C. will reduce flowering.

*Time to flower.*—65-85 days.

*Inflorescence longevity on the plant.*—Inflorescence will maintain good color and substance for about 5-10 days; however, the longevity of individual inflorescence is highly dependent on temperature and light conditions. Inflorescence persistent.

*Quantity of inflorescences heads.*—Freely flowering; about 32 buds and open inflorescences per plant.

*Fragrance.*—Sweet, fresh and very discreet.

*Bud* (*Inflorescences head*).—Rate of opening (from showing color to fully open flower): 1-5 days. The rate of opening is highly dependent on temperature and light conditions. Length: About 12 mm. Diameter: About 10 mm. Shape: Acuminate. Texture: Pubescent with small hairs. Color: RHS 144A at base to 139B at apex.

*Peduncle.*—From both terminate and axillary shoots. Length: About 8-10 cm. Diameter: About 2 mm. Angle: About 0-30° from vertical. Strength: Stiff and strong. Texture: Pubescent with small white hairs. Color: RHS 138A.

*Inflorescence head.*—Length: About 10 mm. Diameter: About 7.5 cm.

*Ray florets.*—Quantity per Inflorescence head: 20-22. Length: 35 mm. Widths: 9-11 mm. Overall shape: Spatulate. Shape at apex: Obtuse. Shape at base: Acute. Margin: Entire, small cleft at apex. Texture: Upper surface: smooth, matt, slightly furrowed. Lower surface: smooth, matt slightly furrowed. Color upper side: RHS Purple N78C. The inner third is grading into white. Color underside: Stripes in various violet colors RHS Violet 85A to Violet 86A.

*Disk florets*.—Quantity per Inflorescence head: 80-100. Length: 6 mm. Diameter: 1 mm. Color Tip: RHS Violet-blue 94A. Center: RHS Purple N78D. Base: White.

*Phyllary*.—20-24. Length: 7-10 mm. Width: 1-2 mm. Overall shape: Lanceolate. Apix: Narrow Acuminate. Base: Fused. Margin: Entire. Color: RHS Green 137C.

Reproductive organs:

*Androecium*.—Location: Disk florets only. Stamen number: 5 fused. Stamen length: About 2 mm. Anther shape: Linear, fused. Anther length: About 2 mm. Pollen amount: Small amount. Pollen color: RHS N25D.

*Gynoecium*.—Location: Ray and disk florets. Quantity: 1. Pistil length: About 4 mm. Stigma shape: Brush-like, cleft 1.5 mm deep. Stigma length: About 1.5 mm. Stigma color: RHS 103A. Style length: About 2 mm. Style color: RHS 103C. Ovary color: RHS 144D.

Seed/fruit: Seed and fruit production has not been observed.

Disease/pest resistance: Resistance to pathogens and pests common to *Osteospermum* has not been observed.

Disease/pest susceptibility: Susceptibility to pathogens and pests common to *Osteospermum* has not been observed.

Temperature tolerance: Plants of the new *Osteospermum* have exhibited good tolerance to rain, wind and drought; however, flowering may cease during hot periods (temperatures above 25° C.). Low temperature tolerance to 1° C.

What is claimed is:

1. A new and distinct cultivar of *Osteospermum* plant named 'DAOSTOOGTYVE', as illustrated and described herein.

* * * * *